United States Patent
Kim et al.

(10) Patent No.: US 10,058,510 B2
(45) Date of Patent: Aug. 28, 2018

(54) PHARMACEUTICAL COMPOSITION OF APREPITANT

(71) Applicants: Daewoong Pharmaceutical Co., Ltd., Seongnam-si, Gyeonggi-do (KR); Bio-Synectics Inc., Seoul (KR)

(72) Inventors: Sanghee Kim, Gwacheon-si (KR); Hee Chul Chang, Seoul (KR); Ji Hoon Jung, Yongin-si (KR)

(73) Assignees: Daewoong Pharmaceutical Co., Ltd., Gyeonggi-Do (KR); Bio-Synectics Inc., Geumchun-Gu, Seoul (KR)

( * ) Notice: Subject to any disclaimer, the term of this patent is extended or adjusted under 35 U.S.C. 154(b) by 0 days.

(21) Appl. No.: 15/542,550

(22) PCT Filed: Jan. 14, 2016

(86) PCT No.: PCT/KR2016/000398
§ 371 (c)(1),
(2) Date: Jul. 10, 2017

(87) PCT Pub. No.: WO2016/114602
PCT Pub. Date: Jul. 21, 2016

(65) Prior Publication Data
US 2018/0000741 A1   Jan. 4, 2018

(30) Foreign Application Priority Data
Jan. 14, 2015   (KR) .................. 10-2015-0006561

(51) Int. Cl.
*A61K 9/48* (2006.01)
*A61K 31/5377* (2006.01)
(Continued)

(52) U.S. Cl.
CPC .............. *A61K 9/4858* (2013.01); *A61K 9/10* (2013.01); *A61K 9/1617* (2013.01);
(Continued)

(58) Field of Classification Search
CPC .... A61K 31/5377; A61K 9/10; A61K 9/1617; A61K 9/4808; A61K 9/4858; A61K 9/4866
See application file for complete search history.

(56) References Cited

U.S. PATENT DOCUMENTS

| 5,145,682 A | 9/1992 | Chien et al. |
|---|---|---|
| 5,719,147 A | 2/1998 | Dorn et al. |

(Continued)

FOREIGN PATENT DOCUMENTS

| CN | 102379845 A | 3/2012 |
|---|---|---|
| JP | 2006-512409 A | 4/2006 |
| KR | 2008-0089659 A | 10/2008 |

OTHER PUBLICATIONS

International Search Report PCT/ISA/210 for International Application No. PCT/KR2016/000398 dated Jun. 24, 2016.

*Primary Examiner* — Savitha M Rao
(74) *Attorney, Agent, or Firm* — Harness, Dickey & Pierce, P.L.C.

(57) ABSTRACT

Disclosed herein a pharmaceutical composition comprising aprepitant a pharmaceutically acceptable salt thereof; at least one hydrocarbon derivative selected from among a fatty acid of 14 to 18 carbon atoms, and a fatty alcohol of 14 to 18 carbon atoms; and at least one selected from among polyoxyethyelene-type nonionic surfactant, sucrose fatty acid ester, and Macrogol 15 hydroxystearate. The pharmaceutical composition of the present disclosure can release aprepitant or a pharmaceutically acceptable salt thereof to effectively exert the pharmaceutical efficacy, and can be dissolved in a fasted state simulated gastrointestinal fluid so that it can be useful for study on the in vivo pharmacokinetic behavior of aprepitant.

10 Claims, 3 Drawing Sheets

(51) Int. Cl.
    *A61K 9/10*        (2006.01)
    *A61K 9/16*        (2006.01)

(52) U.S. Cl.
    CPC .......... *A61K 9/4808* (2013.01); *A61K 9/4866* (2013.01); *A61K 31/5377* (2013.01)

(56) References Cited

U.S. PATENT DOCUMENTS

| | | |
|---|---|---|
| 7,939,098 B2 | 5/2011 | Pauletti et al. |
| 8,258,132 B2 | 9/2012 | Bosch et al. |
| 9,227,958 B2 | 1/2016 | Sawant et al. |
| 2003/0219472 A1 | 11/2003 | Pauletti et al. |
| 2004/0151774 A1 | 8/2004 | Pauletti et al. |
| 2004/0214746 A1 | 10/2004 | Bosch et al. |
| 2009/0192161 A1 | 7/2009 | Sawant et al. |
| 2009/0209541 A1 | 8/2009 | Jain et al. |
| 2011/0009362 A1 | 1/2011 | Joshi et al. |
| 2011/0224147 A1 | 9/2011 | Goodchild |

PHARMACEUTICAL COMPOSITION OF APREPITANT

CROSS-REFERENCE TO RELATED APPLICATIONS

This application is a national phase under 35 U.S.C. § 371 of PCT International Application No. PCT/KR2016/000398 which has an International filing date of Jan. 14, 2016, which claims priority to Korean Application No. 10-2015-0006561, filed Jan. 14, 2015, the entire contents of each of which are hereby incorporated by reference.

TECHNICAL FIELD

The present invention relates to a novel pharmaceutical composition, and more particularly, to a pharmaceutical composition from which aprepitant or a pharmaceutically acceptable salt thereof is effectively released.

BACKGROUND ART

Acting as a tachykinin receptor antagonist, aprepitant is used as a drug for treating and preventing nausea and vomiting.

It has furthermore been suggested that tachykinin receptor antagonists have utility in the treatment of anxiety, depression, anxiety-related diseases, dysthymic disorders, chronic obstructive airways disease, hypersensitivity disorders, vasospastic diseases, fibrosing and collagen diseases (U.S. Pat. No. 5,719,147).

However, aprepitant is difficult to subject into formulation because of its low solubility, and thus research has been directed toward solutions to the problem.

For example, nanoparticles of aprepitant with improved bioavailability are made by wet milling in the presence of an anti-flocculant, and a formulation of the nanoparticles of aprepitant is sold (under the brand name of Emend) (U.S. Pat. Nos. 5,145,684 and 8,258,132).

However, such formulations of conventional techniques bear problems of process complexity, likelihood of contamination, concerns associated with poor drug stabilization, and low efficacy.

Meanwhile, a study on the in vivo pharmacokinetics of a drug without dietary influence needs the dissolution of the drug before meals (e.g., fasted state simulated gastrointestinal fluid with a pH of 4.0), however, nowhere has the dissolution of aprepitant in a fasted state simulated gastrointestinal fluid been found in previous studies.

RELATED ART DOCUMENT

Patent Document (Patent Document 1) U.S. Pat. No. 5,719,147, claims
(Patent Document 2) U.S. Pat. No. 5,145,684, claims
(Patent Document 3) U.S. Pat. No. 8,258,132, claims

DISCLOSURE OF INVENTION

Technical Problem

The object of the present disclosure is to provide a novel pharmaceutical composition that can effectively release aprepitant or a pharmaceutically acceptable salt thereof even in a fasted state simulated gastrointestinal fluid.

The objects of the present invention are not limited to those mentioned above, and other objects, advantages and features of the present invention should be clearly understandable by those skilled in the art from the following description.

Solution to Problem

In accordance with an aspect thereof, the present disclosure provides a pharmaceutical composition comprising aprepitant or a pharmaceutically acceptable salt thereof; at least one hydrocarbon derivative selected from among a fatty acid of 14 to 18 carbon atoms, and a fatty alcohol of 14 to 18 carbon atoms; and at least one surfactant selected from among a polyoxyethyelene-type nonionic surfactant, a sucrose fatty acid ester, and Macrogol 15 hydroxystearate.

The polyoxyethyelene-type nonionic surfactant may be at least one selected from among polyoxyethyelene sorbitan fatty acid ester, polyoxyethyelene alkyl ether, and a polyoxyethyelene castor oil derivative.

In the pharmaceutical composition, the hydrocarbon derivative and the surfactant may each be contained in amounts of 0.01~500 parts by weight, based on 100 parts by weight of aprepitant or a pharmaceutically acceptable salt thereof.

The surfactant may be in a formulation of granules.

The hydrocarbon derivative, and the aprepitant or a pharmaceutically acceptable salt thereof may both be in a formulation of granules.

In the pharmaceutical composition, the hydrocarbon derivative, and the aprepitant or a pharmaceutically acceptable salt thereof may both be in a solid dispersion.

The pharmaceutical composition may be in a pharmaceutical formulation.

In this regard, the pharmaceutical formulation may be a capsule or a tablet.

The capsule may contain therein the surfactant in a granular form, and both the hydrocarbon derivative and the aprepitant or a pharmaceutically acceptable salt thereof in a form of a solid dispersion.

The capsule may contain therein the surfactant in a granular form, and both the hydrocarbon derivative and the aprepitant or a pharmaceutically acceptable salt thereof in a granular form.

The fatty acid may be at least one selected from among myristoleic acid, palmitoleic acid, sapienic acid, oleic acid, elaidic acid, vaccenic acid, linoleic acid, linoelaidic acid, α-linolenic acid, myristic acid, palmitic acid, and stearic acid.

The fatty alcohol may be at least one selected from among myristyl alcohol, pentadecyl alcohol, cetyl alcohol, palmitoleyl alcohol, heptadecyl alcohol, stearyl alcohol, isostearyl alcohol, elaidyl alcohol, oleyl alcohol, linoleyl alcohol, elaidolinoleyl alcohol, linolenyl alcohol, elaidolinolenyl alcohol, ricinoleyl alcohol, and cetearyl alcohol.

The polyoxyethyelene-type nonionic surfactant may be at least one selected from among polyoxyethyelene sorbitan fatty acid ester, polyoxyethyelene alkyl ether, and a polyoxyethyelene castor oil derivative.

Advantageous Effects of Invention

Releasing aprepitant or a pharmaceutically acceptable salt thereof in a fasted state simulated gastrointestinal fluid as well as in a fed state gastrointestinal fluid, the pharmaceutical composition of the present disclosure guarantees the effective pharmaceutical efficacy and can be useful in the in vivo pharmacokinetics of aprepitant or a pharmaceutically acceptable salt thereof.

MODE FOR THE INVENTION

Advantages and features of the present invention, and method to achieve them of the present invention will be obvious with reference to embodiments along with the accompanying drawings which are described below. Meanwhile, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The term 'aprepitant', as used herein, is intended to encompass aprepitant in the form of a free base, and may be represented by the following Chemical Formula I.

[Chemical Formula I]

The term 'a fasted state simulated gastrointestinal fluid', as used herein, is intended to encompass water and/or buffer solution with pH 1.2, 4.0, and/or 6.8 simulating a fasted state of stomach and/or small intestine.

In some embodiments of the present disclosure, the pharmaceutical composition may comprise aprepitant or a pharmaceutically acceptable salt thereof, a hydrocarbon derivative, and a surfactant.

For use in the present disclosure, the aprepitant or a pharmaceutically acceptable salt thereof may be commercially available (Cas No.: 170729-80-3), or may be prepared using a method well known in the art. For instance, it may be prepared using one of the methods disclosed in U.S. Pat. Nos. 5,719,147, 5,145,684, and 8,258,132, or a modification thereof.

The hydrocarbon derivative may be selected from among a fatty acid of 14 to 18 carbon atoms, a fatty alcohol of 14 to 18 carbon atoms, and a combination thereof.

The fatty acid of 14 to 18 carbon atoms may be saturated or unsaturated. Within the scope of such fatty acids myristoleic acid, palmitoleic acid, sapienic acid, oleic acid, elaidic acid, vaccenic acid, linoleic acid, linoelaidic acid, α-linolenic acid, myristic acid, palmitic acid, and/or stearic acid, with preference for myristic acid and/or stearic acid may fall.

As for the fatty acid alcohol of 14 to 18 carbon atoms, its examples include myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z, 12Z-octadecadien-1-ol), elaidolinoleyl alcohol (9E, 12E-octadecadien-1-ol), linolenyl alcohol (9Z, 12Z, 15Z-octadecatrien-1-ol), elaidolinolenyl alcohol (9E, 12E, 15E-octadecatrien-1-ol), ricinoleyl alcohol (12-hydroxy-9-octadecen-1-ol), and/or cetearyl alcohol, with preference for myristyl alcohol, cetyl alcohol, stearyl alcohol, and/or cetearyl alcohol.

As a surfactant useful in the present disclosure, at least one selected from among polyoxyethyelene-type nonionic surfactant, sucrose fatty acid ester, and Macrogol 15 hydroxystearate may be used.

The polyoxyethyelene-type nonionic surfactant means a surfactant having polyoxyethyelene as a non-ionic, hydrophilic group, as exemplified by one or more of polyoxyethyelene sorbitan fatty acid ester, polyoxyethyelene alkyl ether, and a polyoxyethyelene castor oil derivative.

For the polyoxyethyelene sorbitan fatty acid ester, polysorbates 20~85 may be enumerated. In detail, the polyoxyethyelene sorbitan fatty acid ester may be at least one selected from among polysorbate 20, polysorbate 40, polysorbate 60, polysorbate 65, polysorbate 80, and polysorbate 85.

Examples of the polyoxyethyelene alkyl ether include Cetomacrol 1000, polyoxyl 6 cetostearyl ether, polyoxyl 20 cetostearyl ether, polyoxyl 25 cetostearyl ether, polyoxyl 2 cetyl ether, polyoxyl 10 cetyl ether, polyoxyl 20 cetyl ether, polyoxyl 4 lauryl ether, polyoxyl 9 lauryl ether, polyoxyl 23 lauryl ether, polyoxyl 2 oleyl ether, polyoxyl 10 oleyl ether, polyoxyl 20 oleyl ether, polyoxyl 2 stearyl ether, polyoxyl 10 stearyl ether, polyoxyl 20 stearyl ether, and/or polyoxyl 100 stearyl ether.

The polyoxyethyelene castor oil derivative may be selected from among polyoxyl 5 castor oil, polyoxyl 9 castor oil, polyoxyl 15 castor oil, polyoxyl 35 castor oil, polyoxyl 40 castor oil, polyoxyl 60 castor oil, polyoxyl 100 castor oil, polyoxyl 200 castor oil, polyoxyl 60 hydrogenated castor oil, polyoxyl 100 hydrogenated castor oil, polyoxyl 200 hydrogenated castor oil, and a combination thereof.

Preferably, the surfactant may be polysorbate 60, and/or polysorbate 80.

In some embodiments, the pharmaceutical composition may comprise the hydrocarbon derivative in an amount of 0.01~500 parts by weight and the surfactant in an amount of 0.01~500 parts by weight, based on 100 parts by weight of aprepitant or a pharmaceutically acceptable salt thereof. In particular embodiments, 0.01~100 parts by weight of the hydrocarbon derivative, and 0.01~100 parts by weight of the surfactant may be used based on 100 parts by weight of aprepitant or a pharmaceutically acceptable salt thereof. Aprepitant or a pharmaceutically acceptable salt thereof may be insufficiently released when the hydrocarbon derivative or the surfactant is used in an amount less than the lower limit while the pharmaceutical composition is difficult to formulate into tablets or capsules when the hydrocarbon derivative or the surfactant is used in an amount greater than the upper limit.

The pharmaceutical composition may be in the form of an end product or a semi-product.

Further, the pharmaceutical composition may be obtained by simply admixing aprepitant or a pharmaceutically acceptable salt thereof, the hydrocarbon derivative, and the surfactant, by mixing respective formulations of the ingredients, or by mixing the ingredients after at least one of the ingredients is formulated into a preparation.

For example, the surfactant may be formulated into granules. In this regard, the hydrocarbon derivative, and aprepitant or a pharmaceutically acceptable salt thereof may be also formulated into granules. Alternatively, the hydrocarbon derivative, and aprepitant or a pharmaceutically acceptable salt thereof may be formulated into a solid dispersion.

When one or more of the ingredients are formulated before admixing, the pharmaceutical composition can be prepared easily and can more effectively release aprepitant or a pharmaceutically acceptable salt thereof.

According to some embodiments, the pharmaceutical composition may be in a pharmaceutical formulation per se, such as a tablet, a capsule, etc.

For example, a capsule preparation showing an improved release effect may be easily obtained by formulating the surfactant formulated into granules, and the hydrocarbon derivative, and aprepitant or a pharmaceutically acceptable salt thereof into a solid dispersion, and loading the granules together with the solid dispersion into a capsule.

In an alternative embodiment, a capsule preparation may be obtained by formulating the surfactant into granules, and both the hydrocarbon derivative and aprepitant or a pharmaceutically acceptable salt thereof into granules, and loading all of the granules into a capsule.

For the convenience of formulation, the pharmaceutical composition may further comprise a hydrophilic polymer and/or a sugar alcohol as an additive for enhancing the release of aprepitant or a pharmaceutically acceptable salt thereof. In addition, the pharmaceutical composition may further comprise an additive useful for the formulation into a tablet or a capsule, and/or a lubricant.

The hydrophilic polymer may be at least one selected from among hydroxypropylmethyl cellulose (HPMC, Shin-Etsu), hydroxypropylcellulose (HPC, Shin-Etsu), polyvinyl pyrrolidone (PVP, BASF), polyvinyl alcohol (PVA, Nippon Gohsei), polyethylene glycol (PEG), polyethylene glycol polyvinyl alcohol ester (Brand name: Kollicoat IR, BASF), dextrin (Chemos), cyclodextrin (CyD, ISP), and maltodextrin (brand name: Glucidex, Roquette). Preferable may be hydroxypropylmethyl cellulose and/or polyvinyl pyrrolidone. The hydrophilic polymers may be used alone or in combination, and may be contained in an amount of 1 to 1,000 parts by weight, based on 100 parts by weight of aprepitant or a pharmaceutically acceptable salt thereof, and preferably in an amount of 10 to 500 parts by weight. The hydrophilic polymer may not be homogeneously mixed or combined with aprepitant or a pharmaceutically acceptable salt thereof when used in an amount less than the lower limit, or may make oral administration difficult when its amount exceeds the upper limit.

Examples of the sugar alcohol include mannitol, sorbitol, mannose, and/or xylitol, with preference for mannitol. The sugar alcohols may be used alone or in combination, and may be added in an amount of 1 to 1,000 parts by weight, based on 100 parts by weight of aprepitant or a pharmaceutically acceptable salt thereof, and preferably in an amount of 10 to 500 parts by weight. At an amount less than the lower limit, the sugar alcohol cannot be handled with ease, and an amount greater than the upper limit makes the oral administration of the pharmaceutical composition difficult.

Granulation of the ingredients may be achieved by compressing a mixture of the ingredient under a roller, or by wet-, dry- or melt-granulation, melt congelation, or extrusion.

In addition, the solid dispersion may be prepared using a solvent evaporation method or co-melting method.

According to some embodiments of the present disclosure, the pharmaceutical composition may be a simple mixture of aprepitant or a pharmaceutically acceptable salt thereof, the hydrocarbon derivative, and the surfactant, or may prepared into a hard capsule or tablet by loading powder or granules of the ingredient plus a pharmaceutically acceptable additive, such as a disintegrant, an expedient, a lubricant, etc., into a capsule or by compressing the powder or granule. If necessary, the pharmaceutical composition may be coated using a typical method.

With regard to other formulation methods known in the art, reference may be made to Remington's Pharmaceutical Science (latest edition), Mack Publishing Company, Easton Pa.

As such, the pharmaceutical composition of the present disclosure may be formulated into a preparation suitable for use in the treatment or prevention of vomiting, depression, anxiety-related disorders, etc.

The active ingredient aprepitant or a pharmaceutically acceptable salt thereof may be administered in an amount known to those skilled in the art, and its single dose may range 80 to 125 mg for adults.

A better understanding of the present invention may be obtained through the following examples which are set forth to illustrate, but are not to be construed as limiting the present invention. Materials used in the following Examples, Comparative Examples and Test Examples were selected from among commercially available goods of the best quality.

Example 1: Hard Capsule Containing Aprepitant Mixture

TABLE 1

| Ingredient | Content (mg/C) |
| --- | --- |
| Aprepitant, free base | 125 |
| Hydroxypropylmethyl cellulose | 37.5 |
| Mannitol | 150 |
| Myristyl alcohol | 12.5 |
| Crillet 3 | 12.5 |
| Croscamellose sodium | 5 |
| Crospovidone | 10 |
| Total | 352.5 |

A hard capsule containing an aprepitant mix was prepared with the ingredients and contents listed in Table 1.

Polysorbate 60 (Crillet 3, CRODA Inc) was added to ethanol (20 uL per capsule) while stirring, to give a polysorbate 60 solution. Using a high-speed mixer (SM-1, Sejong, Republic of Korea), the polysorbate 60 solution was mixed with mannitol and granulated. The granules were dried, and sieved through a mesh screen. The dry granules thus obtained were mixed with the other ingredients listed in Table 1, and 352.5 mg of the granule mixture containing 125 mg of aprepitant per capsule was loaded to a hard capsule as described in the Capsule Section of General Provisions for Preparations in the Korean Pharmacopoeia.

Example 2: Hard Capsule Containing Aprepitant Mixture

TABLE 2

| Ingredient | Content (mg/C) |
| --- | --- |
| Aprepitant, free base | 125 |
| Hydroxypropylmethyl cellulose | 37.5 |
| Poloxamer | 12.5 |
| Mannitol | 149.3 |
| Myristyl alcohol | 0.7 |
| Polysorbate 80 | 12.5 |
| Croscarmellose sodium | 5 |
| Crospovidone | 10 |
| Total | 352.5 |

A hard capsule containing an aprepitant mix was prepared with the ingredients and contents listed in Table 2.

Polysorbate 80 was added to ethanol (20 uL per capsule) while stirring, to give a polysorbate 80 solution. Using a high-speed mixer, the polysorbate 80 solution was mixed with mannitol, and granulated. The granules were dried, and sieved through a mesh screen. The dry granules thus obtained were mixed with the other ingredients listed in Table 2, and 352.5 mg of the granule mixture containing 125 mg of aprepitant per capsule was loaded to a hard capsule as described in the Capsule Section of General Provisions for Preparations in the Korean Pharmacopoeia.

Example 3: Hard Capsule Containing Aprepitant Mixture

TABLE 3

| Ingredient | Content (mg/C) |
| --- | --- |
| Aprepitant, free base | 125 |
| Hydroxypropylmethyl cellulose | 37.5 |
| Poloxamer | 12.5 |
| Mannitol | 149.3 |
| Myristyl alcohol | 0.7 |
| Brij97 ® | 12.5 |
| Croscarmellose sodium | 5 |
| Crospovidone | 10 |
| Total | 352.5 |

A hard capsule containing an aprepitant mix was prepared with the ingredients and contents listed in Table 3.

Polyoxyl 10 oleyl ether (Brij97® SIGMA-ALDRICH) was added to ethanol (20 uL per capsule) while stirring, to give a polyoxyl 10 oleyl ether solution. Using a high-speed mixer, the polyoxyl 10 oleyl ether solution was mixed with mannitol, and granulated. The granules were dried, and sieved through a mesh screen. The dry granules thus obtained were mixed with the other ingredients listed in Table 3, and 352.5 mg of the granule mixture containing 125 mg of aprepitant per capsule was loaded to a hard capsule as described in the Capsule Section of General Provisions for Preparations in the Korean Pharmacopoeia.

Example 4: Hard Capsule Containing Aprepitant Mixture

TABLE 4

| Ingredient | Content (mg/C) |
| --- | --- |
| Aprepitant, free base | 125 |
| Hydroxypropylmethyl cellulose | 37.5 |
| Poloxamer | 12.5 |
| Mannitol | 149.3 |
| Myristyl alcohol | 0.7 |
| HCO-60 | 12.5 |
| Croscarmellose sodium | 5 |
| Crospovidone | 10 |
| Total | 352.5 |

A hard capsule containing an aprepitant mix was prepared with the ingredients and contents listed in Table 4.

Polyoxyl 60 hydrogenated castor oil (HCO-60, CRODA Inc) was added to ethanol (20 uL per capsule) while stirring, to give a polyoxyl 60 hydrogenated castor oil solution. Using a high-speed mixer, the polyoxyl 60 hydrogenated castor oil solution was mixed with mannitol, and granulated. The granules were dried, and sieved through a mesh screen. The dry granules thus obtained were mixed with the other ingredients listed in Table 4, and 352.5 mg of the granule mixture containing 125 mg of aprepitant per capsule was loaded to a hard capsule as described in the Capsule Section of General Provisions for Preparations in the Korean Pharmacopoeia.

Example 5: Hard Capsule Containing Aprepitant Mixture

TABLE 5

| Ingredient | Content (mg/C) |
| --- | --- |
| Aprepitant, free base | 125 |
| Hydroxypropylmethyl cellulose | 37.5 |
| Poloxamer | 12.5 |
| Mannitol | 149.3 |
| Myristyl alcohol | 0.7 |
| Sugar ester 1570 | 12.5 |
| Croscarmellose sodium | 5 |
| Crospovidone | 10 |
| Total | 352.5 |

A hard capsule containing an aprepitant mix was prepared with the ingredients and contents listed in Table 5.

Sucrose fatty acid ester (Sugar ester 1570, Mitsubishi-Kagaku Foods Corporation) was added to ethanol (20 uL per capsule) while stirring, to give a sucrose fatty acid ester solution. Using a high-speed mixer, the sucrose fatty acid ester solution was mixed with mannitol, and granulated. The granules were dried, and sieved through a mesh screen. The dry granules thus obtained were mixed with the other ingredients listed in Table 5, and 352.5 mg of the granule mixture containing 125 mg of aprepitant per capsule was loaded to a hard capsule as described in the Capsule Section of General Provisions for Preparations in the Korean Pharmacopoeia.

Example 6: Hard Capsule Containing Aprepitant Mixture

TABLE 6

| Ingredient | Content (mg/C) |
|---|---|
| Aprepitant, free base | 125 |
| Hydroxypropylmethyl cellulose | 37.5 |
| Poloxamer | 12.5 |
| Mannitol | 149.3 |
| Myristyl alcohol | 0.7 |
| Solutol HS | 12.5 |
| Croscamellose sodium | 5 |
| Crospovidone | 10 |
| Total | 352.5 |

A hard capsule containing an aprepitant mix was prepared with the ingredients and contents listed in Table 6.

Macrogol 15 hydroxystearate (Solutol HS, BSAF) was added to ethanol (20 uL per capsule) while stirring, to give a Macrogol 15 hydroxystearate solution. Using a high-speed mixer, the Macrogol 15 hydroxystearate solution was mixed with mannitol, and granulated. The granules were dried, and sieved through a mesh screen. The dry granules thus obtained were mixed with the other ingredients listed in Table 6, and 352.5 mg of the granule mixture containing 125 mg of aprepitant per capsule was loaded to a hard capsule as described in the Capsule Section of General Provisions for Preparations in the Korean Pharmacopoeia.

Example 7: Hard Capsule Containing Aprepitant Mixture

TABLE 7

| Ingredient | Content (mg/C) |
|---|---|
| Aprepitant, free base | 125 |
| Hydroxypropylmethyl cellulose | 37.5 |
| Poloxamer | 12.5 |
| Mannitol | 149.3 |
| Stearyl alcohol | 0.7 |
| Polysorbate 80 | 12.5 |
| Croscamellose sodium | 5 |
| Crospovidone | 10 |
| Total | 352.5 |

A hard capsule containing an aprepitant mix was prepared with the ingredients and contents listed in Table 7.

Polysorbate 80 was added to ethanol (20 uL per capsule) while stirring, to give a polysorbate 80 solution. Using a high-speed mixer, the polysorbate 80 solution was mixed with mannitol, and granulated. The granules were dried, and sieved through a mesh screen. The dry granules thus obtained were mixed with the other ingredients listed in Table 7, and 352.5 mg of the granule mixture containing 125 mg of aprepitant per capsule was loaded to a hard capsule as described in the Capsule Section of General Provisions for Preparations in the Korean Pharmacopoeia.

Example 8: Hard Capsule Containing Aprepitant Mixture

TABLE 8

| Ingredient | Content (mg/C) |
|---|---|
| Aprepitant, free base | 125 |
| Hydroxypropylmethyl cellulose | 37.5 |
| Poloxamer | 12.5 |
| Mannitol | 149.3 |
| Myristric acid | 0.7 |
| Polysorbate 80 | 12.5 |
| Croscamellose sodium | 5 |
| Crospovidone | 10 |
| Total | 352.5 |

A hard capsule containing an aprepitant mix was prepared with the ingredients and contents listed in Table 8.

Polysorbate 80 was added to ethanol (20 uL per capsule) while stirring, to give a polysorbate 80 solution. Using a high-speed mixer, the polysorbate 80 solution was mixed with mannitol, and granulated. The granules were dried, and sieved through a mesh screen. The dry granules thus obtained were mixed with the other ingredients listed in Table 8, and 352.5 mg of the granule mixture containing 125 mg of aprepitant per capsule was loaded to a hard capsule as described in the Capsule Section of General Provisions for Preparations in the Korean Pharmacopoeia.

Example 9: Hard Capsule Containing Aprepitant Mixture

TABLE 9

| Ingredient | Content (mg/C) |
|---|---|
| Aprepitant, free base | 125 |
| Hydroxypropylmethyl cellulose | 37.5 |
| Poloxamer | 12.5 |
| Mannitol | 149.3 |
| Stearic acid | 0.7 |
| Polysorbate 80 | 12.5 |
| Croscamellose sodium | 5 |
| Crospovidone | 10 |
| Total | 352.5 |

A hard capsule containing an aprepitant mix was prepared with the ingredients and contents listed in Table 9.

Polysorbate 80 was added to ethanol (20 uL per capsule) while stirring, to give a polysorbate 80 solution. Using a high-speed mixer, the polysorbate 80 solution was mixed with mannitol, and granulated. The granules were dried, and sieved through a mesh screen. The dry granules thus obtained were mixed with the other ingredients listed in Table 9, and 352.5 mg of the granule mixture containing 125 mg of aprepitant per capsule was loaded to a hard capsule as described in the Capsule Section of General Provisions for Preparations in the Korean Pharmacopoeia.

Example 10: Hard Capsule Containing Aprepitant Solid Dispersion

TABLE 10

| Ingredient | Content (mg/C) |
| --- | --- |
| Aprepitant, free base | 125 |
| Hydroxypropylmethyl cellulose | 37.5 |
| Mannitol | 150 |
| Myristyl alcohol | 12.5 |
| Crillet 3 | 12.5 |
| Croscarmellose sodium | 5 |
| Crospovidone | 10 |
| Total | 352.5 |

A hard capsule containing an aprepitant solid dispersion was prepared with the ingredients and contents listed in Table 10.

Aprepitant and myristyl alcohol were added to ethanol (5 mL per capsule) in a vessel on a hot plate, and stirred at 40° C. to give an aprepitant solution.

Separately, hydroxypropylmethyl cellulose and mannitol (30 mg per capsule) were stirred in water (10 mL per capsule) to give a hydroxypropylmethyl cellulose solution.

Then, the aprepitant solution, and the hydroxypropylmethyl cellulose solution were homogeneously mixed into a clear spray drying solution. Using a spray dryer (B-191, Buchi, Switzerland), the spray drying solution was spray dried to produce a solid dispersion. A spray drying condition was set to be 95° C. for the inlet temperature, and 50° C. for the outlet temperature.

Meanwhile, polysorbate 60 (Crillet 3, CRODA Inc) was added to ethanol (20 uL per capsule) while stirring, to give a polysorbate 60 solution. Using a high-speed mixer, the polysorbate 60 solution was added to mannitol (120 mg per capsule), and granulated. The granules were dried, and sieved through a mesh screen. The dry granules thus obtained, and the solid dispersion were mixed with the other ingredients listed in Table 10, and 352.5 mg of the granule mixture containing 125 mg of aprepitant per capsule was loaded to a hard capsule as described in the Capsule Section of General Provisions for Preparations in the Korean Pharmacopoeia.

Example 11: Hard Capsule Containing Aprepitant Granule

TABLE 11

| Ingredient | Content (mg/C) |
| --- | --- |
| Aprepitant, free base | 125 |
| Hydroxypropylmethyl cellulose | 37.5 |
| Mannitol | 150 |
| Myristyl alcohol | 12.5 |
| Crillet 3 | 12.5 |
| Croscarmellose sodium | 5 |
| Crospovidone | 10 |
| Total | 352.5 |

A hard capsule containing an aprepitant granule was prepared with the ingredients and contents listed in Table 11.

Myristyl alcohol was added to ethanol (5 mL per capsule) in a vessel on a hot plate, and stirred at 40° C. to give a myristyl alcohol solution.

A pre-mixture of aprepitant, hydroxypropylmethyl cellulose, and mannitol (30 mg per capsule) was subjected, together with the myristyl alcohol solution, to wet granulation using a high-speed mixer (SM-1, Sejong, Korea), and dried. The dry granules thus obtained were sieved through a mesh screen to produce aprepitant granules.

Meanwhile, polysorbate 60 (Crillet 3, CRODA Inc) was added to ethanol (20 uL per capsule) while stirring, to give a polysorbate 60 solution. Using a high-speed mixer, the polysorbate 60 solution was added to mannitol (120 mg per capsule), and granulated. The granules were dried, and sieved through a mesh screen to produce polysorbate 60 granules.

Then, the aprepitant granules and the polysorbate 60 granules were mixed with the other ingredients listed in Table 11, and 352.5 mg of the granule mixture containing 125 mg of aprepitant per capsule was loaded to a hard capsule as described in the Capsule Section of General Provisions for Preparations in the Korean Pharmacopoeia.

Example 12: Hard Capsule Containing Aprepitant Solid Dispersion

TABLE 12

| Ingredient | Content (mg/C) |
| --- | --- |
| Aprepitant, free base | 125 |
| Hydroxypropylmethyl cellulose | 37.5 |
| Mannitol | 150 |
| Myristyl alcohol | 12.5 |
| Polysorbate 80 | 12.5 |
| Croscarmellose sodium | 5 |
| Crospovidone | 10 |
| Total | 352.5 |

A hard capsule containing an aprepitant solid dispersion was prepared with the ingredients and contents listed in Table 12.

Aprepitant and myristyl alcohol were added to ethanol (5 mL per capsule) in a vessel on a hot plate, and stirred at 40° C. to give an aprepitant solution.

Separately, hydroxypropylmethyl cellulose and mannitol (30 mg per capsule) were stirred in water (10 mL per capsule) to give a hydroxypropylmethyl cellulose solution.

Then, the aprepitant solution, and the hydroxypropylmethyl cellulose solution were homogeneously mixed into a clear spray drying solution. Using a spray dryer (B-191, Buchi, Switzerland), the spray drying solution was spray dried to produce a solid dispersion. A spray drying condition was set to be 95° C. for the inlet temperature, and 50° C. for the outlet temperature.

Meanwhile, polysorbate 80 was added to ethanol (20 uL per capsule) while stirring, to give a polysorbate 80 solution. Using a high-speed mixer, the polysorbate 80 solution was added to mannitol (120 mg per capsule), and granulated. The granules were dried, and sieved through a mesh screen. The dry granules thus obtained, and the solid dispersion were mixed with the other ingredients listed in Table 12, and 352.5 mg of the granule mixture containing 125 mg of aprepitant per capsule was loaded to a hard capsule as described in the Capsule Section of General Provisions for Preparations in the Korean Pharmacopoeia.

Comparative Example 1: Commercially Available Oral Formulation

Emend 125 mg capsule (MSD, Korea) containing 125 mg of aprepitant was prepared.

Comparative Example 2: Hard Capsule Containing Aprepitant and SLS Surfactant

TABLE 13

| Ingredient | Content (mg/C) |
| --- | --- |
| Aprepitant, free base | 125 |
| Hydroxypropylmethyl cellulose | 37.5 |
| Poloxamer | 12.5 |
| Mannitol | 149.3 |
| Myristyl alcohol | 0.7 |
| Sodium Lauryl sulfate | 12.5 |
| Croscamellose sodium | 5 |
| Crospovidone | 10 |
| Total | 352.5 |

A hard capsule containing aprepitant, and SLS as a surfactant was prepared with the ingredients and contents listed in Table 13.

Sodium laurylsulfate (SLS) was added to ethanol (20 uL per capsule) while stirring to give an SLS solution. Using a high-speed mixer, the SLS solution was mixed with mannitol, and granulated. The granules were dried, and sieved through a mesh screen. The dry granules thus obtained were mixed with the other ingredients listed in Table 13, and 352.5 mg of the granule mixture containing 125 mg of aprepitant per capsule was loaded to a hard capsule as described in the Capsule Section of General Provisions for Preparations in the Korean Pharmacopoeia.

Comparative Example 3: Hard Capsule Containing Aprepitant and SLS Surfactant

TABLE 14

| Ingredient | Content (mg/C) |
| --- | --- |
| Aprepitant, free base | 80 |
| Hydroxypropylmethyl cellulose | 24 |
| Mannitol | 80 |
| Myristic acid | 8 |
| Sodium laurylsulfate | 33 |
| Croscamellose sodium | 60 |
| Crospovidone | 8 |
| Total | 293 |

A hard capsule containing aprepitant, and SLS as a surfactant was prepared with the ingredients and contents listed in Table 14.

Sodium laurylsulfate (SLS) was added to ethanol (20 uL per capsule) while stirring to give an SLS solution. Using a high-speed mixer, the SLS solution was mixed with mannitol, and granulated. The granules were dried, and sieved through a mesh screen. The dry granules thus obtained were mixed with the other ingredients listed in Table 14, and 293 mg of the granule mixture containing 80 mg of aprepitant per capsule was loaded to a hard capsule as described in the Capsule Section of General Provisions for Preparations in the Korean Pharmacopoeia.

Comparative Example 4: Hard Capsule Containing Aprepitant and SLS Surfactant

TABLE 15

| Ingredient | Content (mg/C) |
| --- | --- |
| Aprepitant, free base | 80 |
| Hydroxypropylmethyl cellulose | 24 |
| Mannitol | 80 |
| Palmitic acid | 8 |
| Sodium laurylsulfate | 33 |
| Croscamellose sodium | 60 |
| Crospovidone | 8 |
| Total | 293 |

A hard capsule containing aprepitant, and SLS as a surfactant was prepared with the ingredients and contents listed in Table 15.

Sodium laurylsulfate (SLS) was added to ethanol (20 uL per capsule) while stirring to give an SLS solution. Using a high-speed mixer, the SLS solution was mixed with mannitol, and granulated. The granules were dried, and sieved through a mesh screen. The dry granules thus obtained were mixed with the other ingredients listed in Table 15, and 293 mg of the granule mixture containing 80 mg of aprepitant per capsule was loaded to a hard capsule as described in the Capsule Section of General Provisions for Preparations in the Korean Pharmacopoeia.

Comparative Example 5: Hard Capsule Containing Aprepitant and Lacking Hydrocarbon Derivative

TABLE 16

| Ingredient | Content (mg/C) |
| --- | --- |
| Aprepitant, free base | 125 |
| Hydroxypropylmethyl cellulose | 37.5 |
| Poloxamer | 12.5 |
| Mannitol | 150 |
| Crillet 3 | 12.5 |
| Croscamellose sodium | 5 |
| Crospovidone | 10 |
| Total | 352.5 |

An aprepitant-containing hard capsule free of a hydrocarbon derivative was prepared with the ingredients and contents listed in Table 16.

Polysorbate 60 (Crillet 3, CRODA Inc) was added to ethanol (20 uL per capsule) while stirring to give a polysorbate 60 solution. Using a high-speed mixer, the polysorbate 60 solution was mixed with mannitol, and granulated. The granules were dried, and sieved through a mesh screen.

The dry polysorbate 60 granules thus obtained were mixed with the other ingredients listed in Table 16, and 352.5 mg of the granule mixture containing 125 mg of aprepitant per capsule was loaded to a hard capsule as described in the Capsule Section of General Provisions for Preparations in the Korean Pharmacopoeia.

Comparative Example 6: Hard Capsule Containing Aprepitant and Lacking Hydrocarbon Derivative

TABLE 17

| Ingredient | Content (mg/C) |
|---|---|
| Aprepitant, free base | 125 |
| Hydroxypropylmethyl cellulose | 37.5 |
| Poloxamer | 12.5 |
| Mannitol | 150 |
| Polysorbate 80 | 12.5 |
| Croscarmellose sodium | 5 |
| Crospovidone | 10 |
| Total | 352.5 |

An aprepitant-containing hard capsule free of a hydrocarbon derivative was prepared with the ingredients and contents listed in Table 17.

Polysorbate 80 was added to ethanol (20 uL per capsule) while stirring to give a polysorbate 80 solution. Using a high-speed mixer, the polysorbate 80 solution was mixed with mannitol, and granulated. The polysorbate 80 granules thus obtained were dried, and sieved through a mesh screen.

The dry polysorbate 80 granules were mixed with the other ingredients listed in Table 17, and 352.5 mg of the granule mixture containing 125 mg of aprepitant per capsule was loaded to a hard capsule as described in the Capsule Section of General Provisions for Preparations in the Korean Pharmacopoeia.

Test Example 1: Dissolution Test

Formulations prepared in the Examples and Comparative Examples were tested for dissolution. As dissolution media for the dissolution test, water, a 2.2% aqueous sodium laurylsulfate solution, water pH 4.0, and water pH 6.8 were used. At regular time intervals after dissolution started, samples were taken, and analyzed by HPLC. Peak areas accounted for amounts of the dissolved aprepitant. More details are as follows.

Dissolution tester: Vankel VK-7020S

Dissolution medium 1: 2.2% sodium lauryl sulfate (SLS) solution 900 mL

Dissolution medium 2: purified water 900 mL

Dissolution medium 3: water (pH 6.8) 900 mL

To 250 mL of 0.2 mol/L potassium dihydrogen phosphate was added 118 mL of 0.2 mol/L sodium hydroxide, followed by water to form a total of 900 mL.

Dissolution medium 4: acetate buffer (pH 4.0) 900 mL 0.05 mol/L acetic acid was mixed at a ratio of 41:9 with 0.05 mol/L sodium acetate to give a buffer with pH 4.0.

Rotation speed: 100 rpm for the 2.2% aqueous SLS solution 50 rpm for other than the 2.2% aqueous SLS solution Analysis: HPLC Detector: UV absorption spectrometer (wavelength 210 nm)

Column: Capcell Pak C18 (4.6×250 mm, 5um)

Column Temp.: 35° C.

Mobile phase: 1 L of water was added with 1 ml of phosphoric acid, stirred, and homogenously mixed with 1 L of acetonitrile.

Flow rate: 1.5 mL/min

Dissolution test results are given in Table 18 and FIGS. 1 to 6.

Table 18 summarizes dissolution test results when formulations of Comparative Example 1 and Examples 1 to 12 are dissolved in a 2.2% sodium laurylsulfate aqueous solution.

TABLE 18

| Time (min) | 20 min |
|---|---|
| C. Example 1 | 85.30% |
| Example 1 | 92.34% |
| Example 2 | 92.44% |
| Example 3 | 93.23% |
| Example 4 | 93.80% |
| Example 5 | 83.03% |
| Example 6 | 81.28% |
| Example 7 | 90.56% |
| Example 8 | 91.56% |
| Example 9 | 88.30% |
| Example 10 | 92.54% |
| Example 11 | 96.52% |
| Example 12 | 89.72% |

As shown in Table 18, formulations of Examples 1 to 12 exhibited dissolution rates as high as or higher than that of the commercially available oral formulation of Comparative Example 1.

Figure 1:
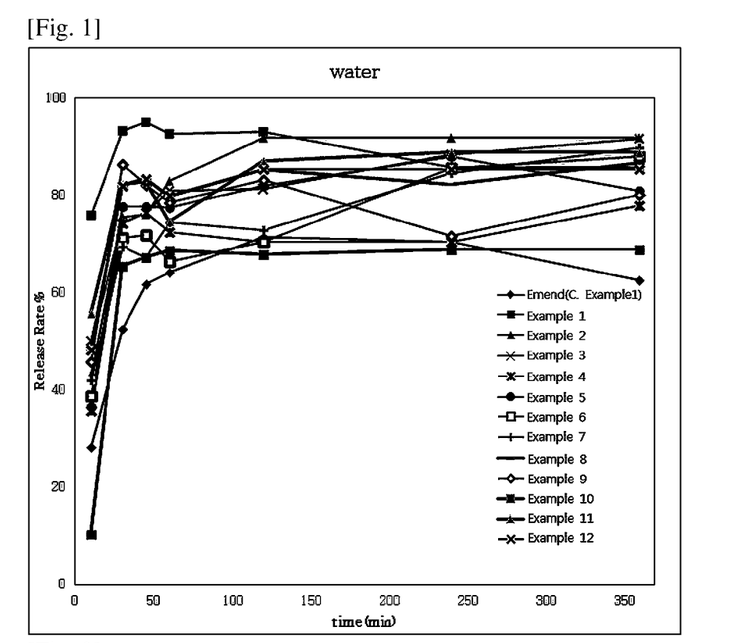
FIG. 1 is a graph showing dissolution test results of formulations of Examples 1 to 12 and Comparative Example 1 against water as a dissolution medium.
Figure 2:
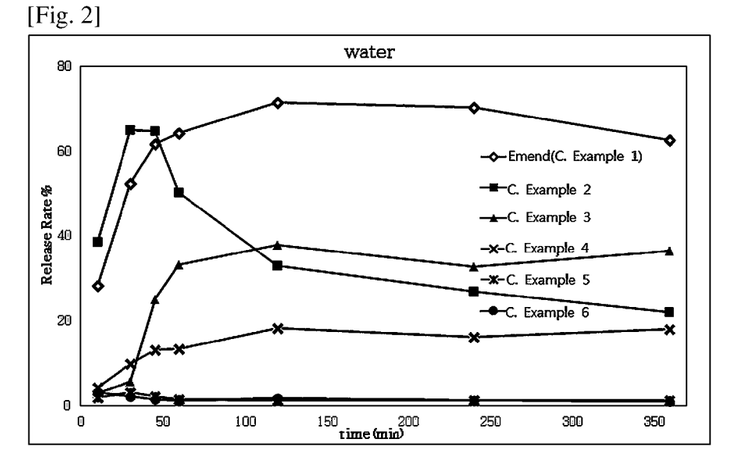
FIG. 2 is a graph showing dissolution test results of formulations of Comparative Examples 1 to 6 against water as a dissolution medium.

FIG. 1 is a graph showing dissolution test results of formulations of Examples 1 to 12 and Comparative Example 1 against water as a dissolution medium, and FIG. 2 is a graph showing dissolution test results of formulations of Comparative Examples 1 to 6 against water as a dissolution medium.

As can be understood from data of FIGS. 1 and 2, formulations of Examples 1 to 12 were observed to release the active ingredient in water as a dissolution medium at dissolution rates as high as or higher than the commercially available oral formulation of Comparative Example 1. Formulations of Comparative Examples 2 to 6, which employed surfactants different from those used in Examples 1 to 6 or lacked a hydrocarbon derivative could not exhibit high dissolution rates against water as a dissolution medium.

Figure 3:
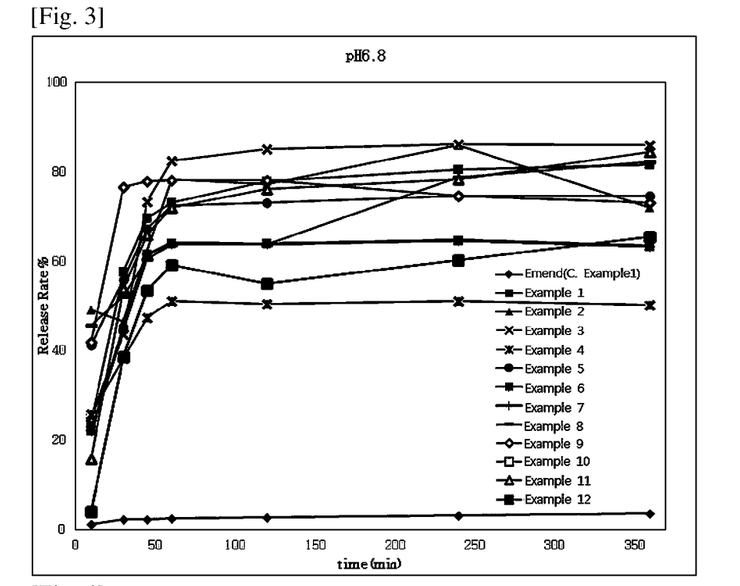
FIG. 3 is a graph showing dissolution test results of formulations of Examples 1 to 12 and Comparative Example 1 against a dissolution medium with a pH of 6.8.
Figure 4:
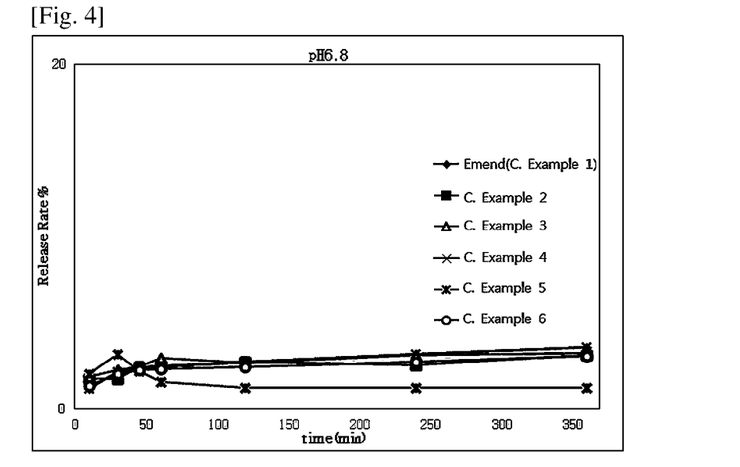
FIG. 4 is a graph showing dissolution test results of formulations of Comparative Examples 1 to 6 against a dissolution medium with a pH of 6.8.

In addition, FIG. 3 is a graph showing dissolution test results of formulations of Examples 1 to 12 and Comparative Example 1 against a dissolution medium with a pH of 6.8, and FIG. 4 is a graph showing dissolution test results of formulations of Comparative Examples 1 to 6 against a dissolution medium with a pH of 6.8.

As can be seen in FIGS. 3 and 4, the formulations of Examples 1 to 12 exhibited high dissolution rates against a fasted state simulated gastrointestinal fluid with a pH of 6.8 whereas the formulations of Comparative Examples 1 to 6 did almost not release aprepitant.

Figure 5:
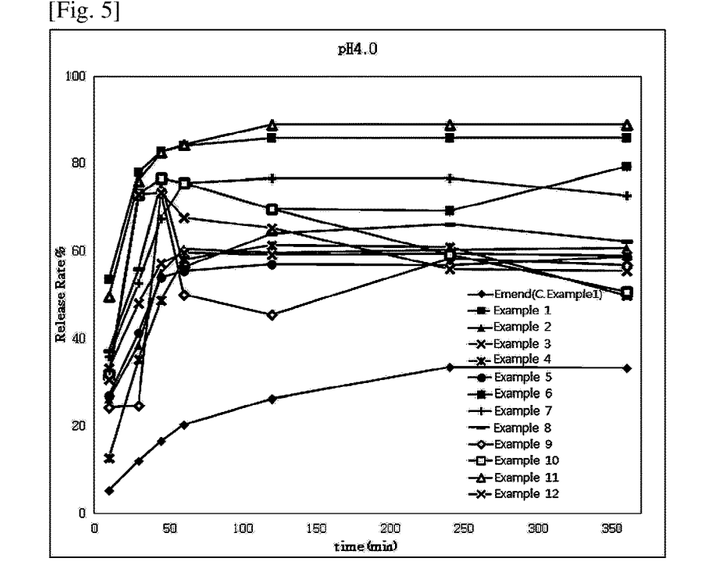
FIG. 5 is a graph showing dissolution test results of formulations of Examples 1 to 12 and Comparative Example 1 against a dissolution medium with a pH of 4.0.
Figure 6:
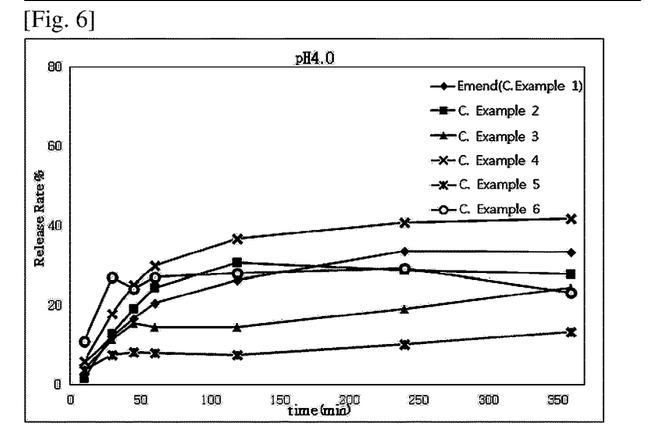
FIG. 6 is a graph showing dissolution test results of formulations of Comparative Examples 1 to 6 against a dissolution medium with a pH of 4.0.

Furthermore, FIG. 5 is a graph showing dissolution test results of formulations of Examples 1 to 12 and Comparative Example 1 against a dissolution medium with a pH of 4.0, and FIG. 6 is a graph showing dissolution test results of formulations of Comparative Examples 1 to 6 against a dissolution medium with a pH of 4.0.

Against a dissolution medium with a pH of 4.0, as shown in FIGS. 5 and 6, the formulations of Examples 1 to 12 were superior in dissolution rate to those of Comparative Examples 1 to 6.

As understood from the data obtained in Test Example 1, the pharmaceutical composition of the present disclosure can effectively release aprepitant against various dissolution media, particularly, even in the fasted state simulated gastrointestinal fluid with a pH of 6.8.

Test Example 2: Pharmacokinetic (PK) Test

A pharmacokinetic test was performed on the capsule of Example 2 as a test drug, with the capsule of Comparative Example 1 serving as a control.

Fourteen male adults were randomly divided into two groups: first and second groups. The capsule of Example 2 was administered to the first group while the capsule of Comparative Example 1 was administered to the second group. On the next day, the capsules of Example 2 and Comparative Example 1 were administered to the second group and the first group, respectively. One capsule was orally administered once a day.

Blood samples were taken with time, and measured for aprepitant concentration. From the measurements, time-concentration curves were constructed, and AUC (Area Under the Curve) and Cmax (Maximum plasma concentration) were obtained.

Figure 7:
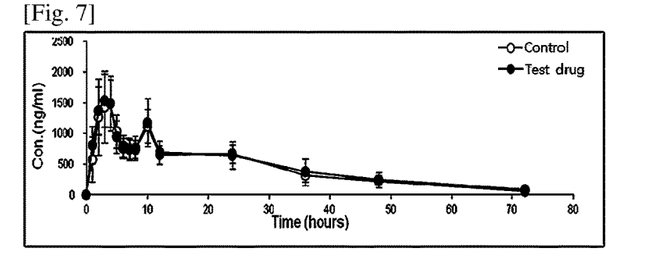
FIG. 7 is a graph showing plasma concentrations with time after oral administration of the capsules of Example 2 and Comparative Example 1.

The results are summarized in Table 19 and are depicted in FIG. 7.

TABLE 19

| | 90% Confidence Interval | | |
|---|---|---|---|
| | Lower limit, 0.8 | Upper limit, 1.25 | T/R Ratio |
| AUC | 0.9428 | 1.1659 | 1.0480 |
| Cmax | 0.8186 | 1.1122 | 0.9540 |

FIG. 7 is a graph showing plasma concentrations with time after oral administration of the capsules of Example 2 and Comparative Example 1.

As shown in Table 19 and FIG. 7, the formulation of Example 2 was almost identical in AUC and Cmax to the commercially available oral formulation.

The pharmaceutical composition of the present disclosure can thus be effectively dissolved, which leads to effective bioavailability.

Taken together, the data obtained above demonstrate that aprepitant or a pharmaceutically acceptable salt thereof, when formulated according to the present disclosure, can be released effectively to exert its pharmaceutical efficacy and can be dissolved even in a fasted state simulated gastrointestinal fluid enough to give information on in vivo pharmacokinetic behavior.

INDUSTRIAL APPLICABILITY

As described hitherto, the pharmaceutical composition of the present disclosure can release aprepitant or a pharmaceutically acceptable salt thereof to effectively exert the pharmaceutical efficacy, and can be dissolved in a fasted state simulated gastrointestinal fluid so that it can be useful for study on the in vivo pharmacokinetic behavior of aprepitant.

Those skilled in the art will understand that the present invention can be implemented as other concrete forms without changing the inventive concept or essential features. Therefore, these embodiments as described above are only proposed for illustrative purposes and do not limit the present invention. It will be apparent to those skilled in the art that a variety of modifications and variations may be made without departing the spirit and scope of the present invention as defined by the appended claims. Further, such modifications and variations should not be understood independently from the technical idea or perspective of the present invention.

The invention claimed is:

1. A pharmaceutical composition, comprising:
   aprepitant or a pharmaceutically acceptable salt thereof;
   at least one hydrocarbon derivative selected from among a fatty acid of 14 to 18 carbon atoms, and a fatty alcohol of 14 to 18 carbon atoms; and
   at least one surfactant selected from among a polyoxyethylene-type nonionic surfactant, a sucrose fatty acid ester, and Macrogol 15 hydroxystearate,
   wherein the pharmaceutical composition is in a pharmaceutical formulation; and
   wherein the pharmaceutical formulation is a capsule or a tablet.

2. The pharmaceutical composition of claim 1, wherein the hydrocarbon derivative and the surfactant are each contained in amounts of 0.01~500 parts by weight, based on 100 parts by weight of aprepitant or a pharmaceutically acceptable salt thereof.

3. The pharmaceutical composition of claim 1, wherein the surfactant is in a formulation of granules.

4. The pharmaceutical composition of claim 1, wherein the hydrocarbon derivative, and the aprepitant or a pharmaceutically acceptable salt thereof are both in a formulation of granules.

5. The pharmaceutical composition of claim 1, wherein the hydrocarbon derivative, and the aprepitant or a pharmaceutically acceptable salt thereof are both in a solid dispersion.

6. The pharmaceutical composition of claim 1, wherein the capsule contains therein the surfactant in a granular form, and both the hydrocarbon derivative and the aprepitant or a pharmaceutically acceptable salt thereof in a form of a solid dispersion.

7. The pharmaceutical composition of claim 1, wherein the capsule contains therein the surfactant in a granular form, and both the hydrocarbon derivative and the aprepitant or a pharmaceutically acceptable salt thereof in a granular form.

8. The pharmaceutical composition of claim 1, wherein the fatty acid is at least one selected from among myristoleic acid, palmitoleic acid, sapienic acid, oleic acid, elaidic acid, vaccenic acid, linoleic acid, linoelaidic acid, α-linolenic acid, myristic acid, palmitic acid, and stearic acid.

9. The pharmaceutical composition of claim 1, wherein the fatty alcohol is at least one selected from among myristyl alcohol, pentadecyl alcohol, cetyl alcohol, palmitoleyl alcohol, heptadecyl alcohol, stearyl alcohol, isostearyl alcohol, elaidyl alcohol, oleyl alcohol, linoleyl alcohol, elaidolinoleyl alcohol, linolenyl alcohol, elaidolinolenyl alcohol, ricinoleyl alcohol, and cetearyl alcohol.

10. The pharmaceutical composition of claim 1, wherein the polyoxyethylene-type nonionic surfactant is at least one selected from among polyoxyethylene sorbitan fatty acid ester, polyoxyethylene alkyl ether, and a polyoxyethylene castor oil derivative.

* * * * *